United States Patent [19]
Russell et al.

[11] 3,961,893
[45] June 8, 1976

[54] STEAM DISINFECTOR FOR CONTACT LENSES

[75] Inventors: James S. Russell; Arthur G. Nelson, both of Rancho Santa Fe, Calif.

[73] Assignee: Hydrotherm Corporation, San Diego, Calif.

[22] Filed: Oct. 17, 1974

[21] Appl. No.: 515,700

[52] U.S. Cl.................................. 21/95; 21/56; 21/92; 21/94; 21/97; 21/118; 21/119; 126/344; 126/348; 126/369; 134/31; 219/362; 219/401
[51] Int. Cl.² ...................... A61L 3/00; H05B 1/00
[58] Field of Search ............................ 21/91-95, 21/97, 56, 118, 119; 219/401, 362, 437, 289; 126/275 E, 348, 344, 369; 134/1, 11, 12, 31

[56] References Cited
UNITED STATES PATENTS

| | | | |
|---|---|---|---|
| 1,348,837 | 8/1920 | Allen | 21/95 |
| 1,613,537 | 1/1927 | Scacchitti | 21/119 |
| 2,370,238 | 2/1945 | Fisher | 219/289 |
| 2,467,337 | 4/1949 | Schnell | 21/95 |
| 2,597,695 | 5/1952 | Braski et al. | 126/275 E |
| 2,675,458 | 4/1954 | Stiles | 126/275 |
| 2,728,962 | 1/1956 | MacLeod | 21/97 |
| 2,818,794 | 1/1958 | Aslesen | 219/401 |
| 3,280,304 | 10/1966 | Shinohara et al. | 219/437 |
| 3,413,440 | 11/1968 | Drugmand | 219/437 |
| 3,585,362 | 6/1971 | Hoogesteger et al. | 219/289 |
| 3,610,880 | 10/1971 | Kreiberg | 219/362 |
| 3,892,945 | 7/1975 | Lerner | 219/437 |

Primary Examiner—Morris O. Wolk
Assistant Examiner—Dale Lovercheck

[57] ABSTRACT

A disinfector for heating and disinfecting contact lenses in which a main plastic housing is provided having a lens well recess from the top thereof dimensioned for receiving a standard lens carrier, and a vented lid covering the well opening. The lens well has a downwardly facing annular recess on the bottom surface thereof for receiving the top edge of an annodized aluminium cup reservoir. The top lid portion is dimensioned for the measurement of water which is poured into the lens well and hence into the aluminium cup reservoir through a plurality of apertures in the bottom of the lens well. These apertures also serve to allow steam from the water in the reservoir to enter the lens well which is in itself a steam compartment. A annular flat electric heater coil is glued to the bottom of the aluminium cup reservoir leaving a circular section exposed in the center thereof. A thermostat switch is attached to the surface of this circular section which opens after the water has boiled away cutting off the power to the heater. The top surface of the main housing and the cap member are each surrounded by an upwardly extending annular lip for moisture retention.

1 Claim, 3 Drawing Figures

STEAM DISINFECTOR FOR CONTACT LENSES

BRIEF DESCRIPTION OF THE INVENTION

The present invention relates to a disinfector and more particularly to a disinfector dimensioned for disinfecting contact lenses.

According to the invention, a disinfector for contact lenses is provided having a heat insulative plastic main housing with a lens well therein dimensioned for receiving a conventional contact lens carrier. The bottom surface of the well has a plurality of apertures therein for receiving steam from a aluminium cup reservoir disposed directly beneath it. A top cap covers the lens well and both the top of the main housing and the top cap is surrounded by a moisture-retaining lip. The reservoir is constructed of annodized aluminium of a very light gauge and has a heat sink effect. The bottom surface of the reservoir carries a flat annular heating coil which covers substantially the entire bottom surface leaving a circular section in the center thereof. A thermostatic switch is attached to the circular center portion being surrounded by the heating coil and is in series with the electrical power to the heating coil. When the water placed in the reservoir has boiled out, this central portion will heat to a level which opens the thermostat switch, cutting off power to the heating coil. A pilot light can be included to indicate the presence or absence of electrical power.

The cap is also a measuring cup for measuring the amount of water which is poured into the lens well and through the apertures in the bottom thereof to the aluminium cup reservoir. Hence, when it is desired to disinfect contact lenses, water is first measured in the top cap, poured into the lens well, and the lens carrier placed in the lens well and the lid placed thereon. The heating coil is energized causing the water in the aluminium cup reservoir to boil which releases steam up through the apertures in the lens well bottom. This continues until the water is boiled out of the aluminium cup reservoir, at which time the temperature raises to the point of opening the thermostat switch, cutting off the power to the heater, and the lens carrier is ready to be removed.

An object of the present invention is the provision of an improved contact lens disinfector.

Another object of the invention is the provision of a contact lens disinfector in which timing is automatic.

A further object of the invention is the provision of an improved contact lens disinfector which is inexpensive to manufacture and assemble and extremely convenient in use.

Other objects and many of the attendant advantages of the present invention will be readily appreciated as the same becomes better understood by reference to the following detailed description when considered in connection with the accompanying drawing in which like reference numerals designate like parts throughout the Figures thereof and wherein.

DETAILED DESCRIPTION OF THE DRAWING

Figure 1:
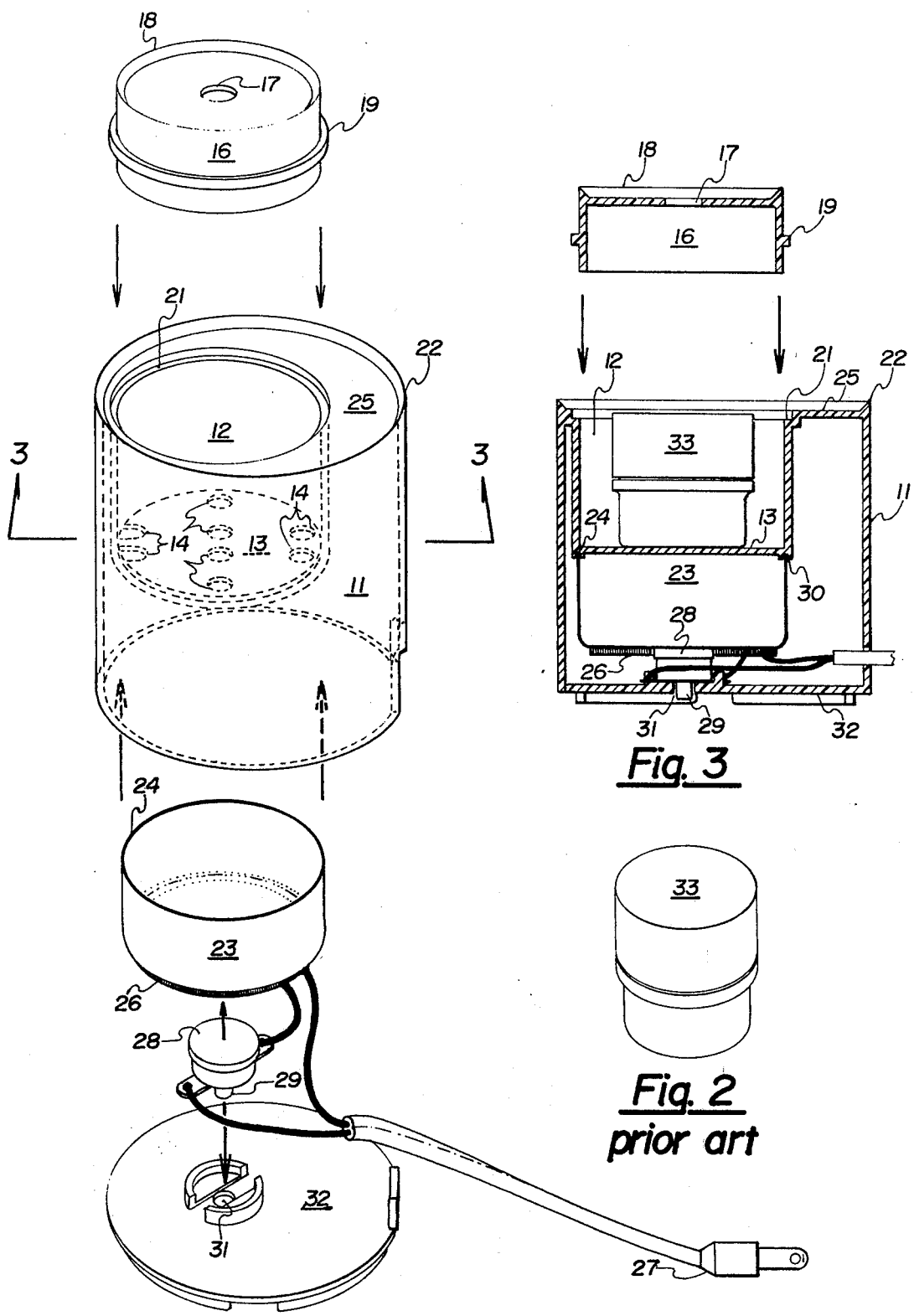
FIG. 1 is an exploded view in perspective of the preferred embodiment of the present invention.

Referring to FIG. 1, a main housing of the present invention is shown at 11 having a contact lens well 12 therein. Lens well 12 has a bottom platform 13 with a plurality of apertures therein. A measuring lid 16 has a vent aperture 17, a moisture retaining lip 18 and an annular restraining extension 19 dimensioned for resting on annular shoulder 21 of main housing 11. Main housing 11 also has a moisture retaining lip 22 around the top edge thereof. Aluminium cup reservoir 23 has a top edge 24 dimensioned for coupling to the bottom surface of platform 13. Flat annular electric heater 26 is carried by the bottom surface of aluminium cup reservoir 23 and is coupled to electric plug 27 through thermostat switch 28. Thermostat switch 28 has a reset button 29 dimensioned for passing through recess aperture 31 of bottom plate 32.

Figure 2:
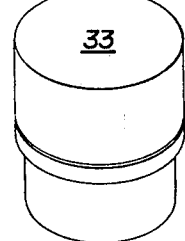
FIG. 2 is a perspective view of a standard contact lens carrier.

Referring to FIG. 2, a typical prior art lens carrier is shown at 33 which is dimensioned to be received by contact lens well 12 of housing 11 (FIG. 1).

Figure 3:
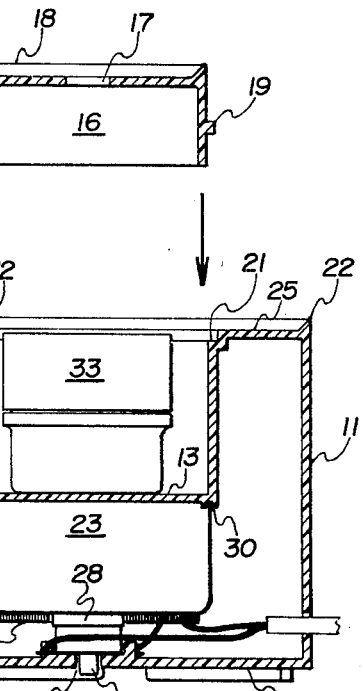
FIG. 3 is a sectional view taken along lines 3 - 3 of FIG. 1 in non-exploded form.

Referring to FIG. 3, main housing 11 has moisture-retaining lip 22 surrounding a top deck 25. Contact lens well 13 extends downwardly therefrom. Shelf 21 is dimensioned for carrying annular extension 19 on top portion 16. Top portion 16 terminates in upwardly extending moisture-retaining lip 18 and has a vent aperture 17 therein. Contact lens carrier 33 is shown resting on platform 13 of lens well 12.

Aluminium cup reservoir 23 has a top edge 24 received by annular groove 30 in the bottom of contact lens well 12. Flat annular electric heater 26 is attached to and carried by the bottom surface of aluminium cup reservoir 23 and surrounds a thermostat switch 28 which is also carried by the bottom surface of aluminium cup reservoir 23. Reset button 29 passes through aperture 31 of bottom plate 32. Bottom plate 32 is carried by main housing 11.

OPERATION

The purpose of the arrangement of parts and selection of materials described above with reference to the drawing is primarily to reduce the size of contact lens disinfectors together with an attendant cost reduction and an increase in convenience. It has been found empirically, for example, that the most efficient reservoir is constructed of a thin-walled aluminium. The type of heater and thermostat cut-off switch were selected for maximum efficiency and minimum size.

The top portion 16 is dimensioned for holding the amount of water necessary to disinfect contact lenses when boiled out in aluminium cup reservoir 23. By holding one's finger over vent aperture 17, this top portion is filled with water poured into reservoir 23. After this has been accomplished, the lenses are placed in lens carrier 33 with the lens carrier in turn placed in reservoir 12. The lens carrier is substantially smaller than the reservoir leaving enough of the apertures 14 exposed to allow steam to pass up through these apertures and around lens carrier 33. When the water has all boiled out through the heating action of electric heater 26, the aluminium cup reservoir 23 acts as a heat sink raising the temperature of thermostat switch 28 to the point where it will open, causing reset button 29 to extend itself, cutting off power to heater 26. At this time the lens carrier 33 is removed and the lenses therein are disinfected. When it is desired to repeat the process, the reset button 29 is depressed thereby closing thermostat switch 28 and the unit is ready for its next cycle.

Because of the unique construction, it has been found that under one ounce of water is necessary and actually two-thirds of an ounce of water is all that is required in reservoir 23. The heater capacity is reduced to under 40 watts, all of which is instrumental in reducing the overall size and cost of the disinfector.

It should be understood, of course, that the foregoing disclosure relates to only a preferred embodiment of the invention and that it is intended to cover all changes and modifications of the example of the invention herein chosen, for the purposes of the disclosure, which do not constitute departures from the spirit and scope of the invention.

The invention claimed is:

1. A disinfector comprising:
    a plastic main housing;
    a recess in said main housing terminating in a bottom platform having upper and lower surfaces, said recess and bottom platform forming a lens well, said lens well dimensioned for receiving a standard lens carrier;
    a plurality of apertures in said bottom platform;
    a metallic reservoir attached to the lower surface of said bottom platform and disposed directly beneath said apertures, said metallic reservoir having a bottom surface;
    a flat annular heating coil carried by and attached to the bottom surface of said metallic reservoir;
    a manually resettable thermostat switch mounted on the bottom surface of said reservoir surrounded by said heating coil and connected electrically in series with said heating coil, said thermostat switch being operable for opening the electrical connection upon an increase in temperature when said reservoir is empty; and
    a cap removably covering said recess whereby upon placing water in said reservoir and placing a lens carrier with contact lenses therein in said well and applying electrical power to said heating coil, boiling water in the reservoir will cause steam to pass through said apertures, heating said lens carrier therein and disinfecting said lenses, said cap being dimensioned for carrying a predetermined volume of water for emptying into said reservoir and disinfecting any contact lens in a lens carrier in the lens well during a period required for boiling out of said predetermined volume of water.

* * * * *